United States Patent [19]

Karol et al.

[11] Patent Number: 5,631,214

[45] Date of Patent: May 20, 1997

[54] PREPARATION OF BISMUTH DITHIOCARBAMATES

[75] Inventors: Thomas J. Karol, Norwalk; Steven G. Donnelly, New Fairfield, both of Conn.

[73] Assignee: R.T. Vanderbilt Company, Inc., Norwalk, Conn.

[21] Appl. No.: 509,277

[22] Filed: Jul. 31, 1995

[51] Int. Cl.$^6$ ................................ C10M 141/12

[52] U.S. Cl. ................ 508/365; 508/283; 508/285; 508/364

[58] Field of Search ................ 508/283, 285, 508/364, 365

[56] References Cited

U.S. PATENT DOCUMENTS

| | | | |
|---|---|---|---|
| 2,400,106 | 5/1946 | Denison et al. | 252/33.6 |
| 2,412,903 | 12/1946 | Miller et al. | 508/364 |
| 2,480,823 | 9/1949 | Morris et al. | 252/42.7 |
| 2,492,314 | 12/1949 | Olin et al. | 260/429 |
| 2,716,089 | 8/1955 | Cyphers et al. | 252/33.6 |
| 2,947,695 | 8/1960 | Leshin et al. | 508/365 |
| 3,139,405 | 6/1964 | Farmer et al. | 252/33.6 |
| 3,707,498 | 12/1972 | Milsom | 508/364 |

*Primary Examiner*—Jerry D. Johnson
*Attorney, Agent, or Firm*—Rasma B. Balodis

[57] ABSTRACT

A novel method is disclosed for preparation of bismuth dithiocarbamates by an exchange reaction between a bismuth carboxylate and a metal dithiocarbamate. The metal dithiocarbamate can be added to the reaction or prepared in situ by reacting a secondary amine and carbon disulfide in the presence of metal oxide, metal hydroxide or a tertiary amine.

The reaction products are useful as extreme pressure additives when incorporated in lubricants.

8 Claims, No Drawings

PREPARATION OF BISMUTH DITHIOCARBAMATES

BACKGROUND OF THE INVENTION

The present invention concerns bismuth dithiocarbamate compounds. More particularly, the invention relates to a novel process for preparing such compounds.

Classically, polyvalent metal salts of dithiocarbamates are prepared by reacting a primary or secondary amine with carbon disulfide and alkali metal hydroxide to form a water soluble intermediate dithiocarbamate salt. This intermediate is reacted with an inorganic polyvalent metal salt to obtain the desired metal dithiocarbamate, often insoluble in water.

It is also known to form polyvalent metal dithiocarbamates by directly reacting primary or secondary amine, carbon disulfide and oxide or hydroxide of the polyvalent metal as described in U.S. Pat. No. 2,492,314.

In another method described in U.S. Pat. No. 2,480,823, polyvalent metal derivatives of organic compounds containing a replaceable hydrogen, e.g. the group -CSSH may be obtained by reacting an inorganic metal salt in liquid ammonia.

Although most polyvalent metal dithiocarbamates can be prepared in economic yields, an exception is bismuth dithiocarbamates. The prior art methods give low yields, even when ammonium media or nitrate salt is employed.

Unexpectedly, it has been discovered that high yields of bismuth dithiocarbamates are obtained by employing a method based on an exchange reaction that is environmentally sound.

SUMMARY OF THE INVENTION

In accordance with the invention, there is provided a novel method for preparation of bismuth dithiocarbamates by an exchange reaction according to the following reaction scheme (I), balanced for a divalent metal dithiocarbamate.

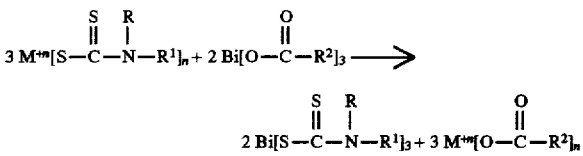

wherein R and $R^1$ are hydrocarbon groups selected independently from alkyl, alkenyl, cycloalkyl, aryl, alkaryl and arylakyl groups and $R^2$ is alkyl and alkenyl group, fatty acid and naphthenic acid radical. In the exchange reaction, M can be a metal with a valence of n=1 or 2.

Alternately, bismuth dithiocarbamates may be prepared directly from a secondary amine and carbon disulfide in the presence of bismuth carboxylate and a metal oxide or hydroxide according to the reaction scheme (II) given below for a divalent metal hydroxide.

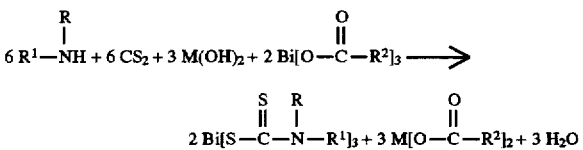

The metal hydroxide or oxide in the reaction scheme (II) will convert the free carboxylic acid to the metal salt either in situ or by post treatment.

The reaction can be also conducted in the presence of an amine in which case the free carboxylic acid will form an amine salt complex.

Another aspect of the invention is the use in lubricant compositions, of a reaction mixture prepared by radical exchange between a metal salt of dihydrocarbyldithiocarbamate and a bismuth carboxylate according to the reaction scheme (I) and (II) hereinabove.

Another object of the invention is the use in lubricating compositions, of a reaction mixture prepared by radical exchange between an amine salt of dihydrocarbyldithiocarbamate and bismuth carboxylate.

DESCRIPTION OF SPECIFIC EMBODIMENTS

The novel method of the invention affords a commercially viable method for the preparation of bismuth dihydrocarbyldithiocarbamates from readily available raw materials. Many dithiocarbamates of monovalent and divalent metals can be prepared in high yields and are relatively inexpensive commercial materials. Similarly, bismuth carboxylates are commercially available. An exchange reaction takes place between the metal dithiocarbamate and the bismuth carboxylate upon heating at about 25° to 1200° C. depending on the starting materials used. The exchange reaction can be conducted in the absence or presence of an inert solvent. Useful solvents are alcohols, acetone, petroleum distillates and mineral spirits.

Metal dithiocarbamates that can be converted by the exchange reaction are represented by the formula

wherein n is 1 to 2; M is a metal atom selected from mono or divalent metals; R and $R^1$ are hydrocarbon groups. Particularly preferred are alkali metals such as sodium and potassium, and metals such as calcium and zinc.

The R and $R^1$ groups are selected independently from alkyl, alkenyl, cycloalkyl, aryl, alkaryl and arylalkyl groups. The alkyl and alkenyl groups may contain up to 22 carbon atoms and higher. Preferred are lower alkyl derivatives containing 1 to 12 carbon atoms.

Exemplary straight chain and branched aliphatic groups, among others, are methyl, ethyl, butyl, propyl, isopropyl, t-butyl, pentyl, hexyl, 2-ethylhexyl, octyl, decyl, decenyl, octadecenyl, cyclopentyl, cyclohexyl, cyclopentenyl, methylcyclohexyl, methylcyclohexenyl, cyclohexenyl, lauryl, stearyl and capryl. Exemplary aryl groups, among others, are phenyl, naphthyl, phenylbutyl, hindered dialkylphenyl, propylphenyl and benzyl.

These metal dithiocarbamates will readily exchange anions with bismuth carboxylates represented by the formula

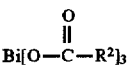

wherein $R^2$ is an alkyl or alkenyl group which may be substituted by alkyl groups or mixtures thereof. Particularly preferred are radicals derived from fatty acids, fatty oils, tall oil and petroleum oxidation products such as naphthenic acid residues.

The reaction mixtures contain about 1:1 to 1.5:1 mole ratio of the bismuth dithiocarbamate to the metal carboxylate.

Alternately, bismuth dithiocarbamates may be prepared directly from a secondary amine and carbon disulfide in the presence of bismuth carboxylate and a metal oxide or hydroxide. In this reaction, the intermediate metal dithiocarbamate is formed in situ and an exchange takes place between the intermediate and the bismuth carboxylate. If metal oxide is not added to the reaction, the ion exchange will take place between the dithiocarbamic alkyl ammonium salt intermediate and bismuth carboxylate. The final reaction mixture then will contain bismuth dithiocarbamate and carboxylic acid. This reaction takes place in an inert solvent such as alcohols, acetone, petroleum distillates and mineral spirits.

In another method, bismuth dithiocarbamates may be prepared directly in the presence of bismuth carboxylate and excess amine. In this reaction, a dialkylammonium dithiocarbamate is formed which then is converted to dialkyl amine salt of carboxylic acid according to the following reaction scheme.

$CS_2 + 2 R-NH-R^1 \longrightarrow$

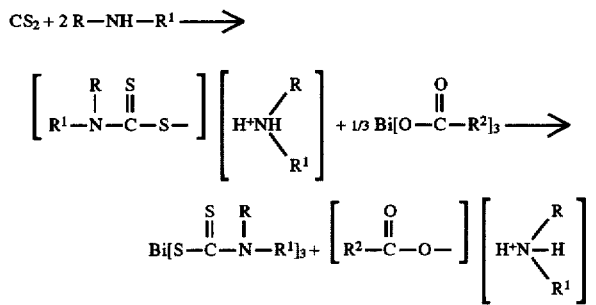

The R, $R^1$ and $R^2$ groups have the same meaning as described hereinabove.

If a reaction mixture of bismuth dithiocarbamate and free carboxylic acid is desired, additional bismuth carboxylate and carbon disulfide can be added to complete the conversion to the carboxylic acid according to the reaction scheme given below.

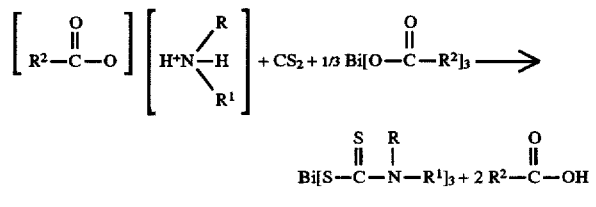

Alternately, the starting material may be a dithiocarbamate acid salt of a tertiary amine having the same or different hydrocarbon substituent groups than the N-substituent groups on the dithiocarbamate and having the formula

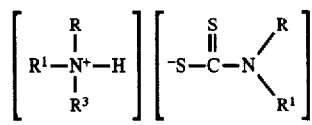

and wherein $R^3$ represents hydrogen R or $R^1$ as defined hereinabove.

Another suitable starting material is the imidazoline salt of the formula

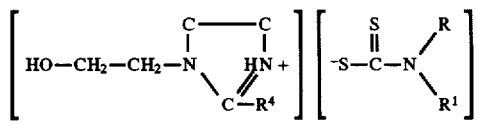

wherein $R^4$ is alkyl, alkenyl or fatty acid residue having 8 to 22 carbon atoms. In the exchange reaction, the amine will be associated with the carboxylic acid upon formation of bismuth dithiocarbamate.

Besides producing high yields, this method produces a reaction mixture that can be used without separation of the bismuth dithiocarbamate in certain applications. That is, the reaction yields by-products that are useful in petroleum applications and that are not disposable waste. Of particular advantage in the production of lubricating oils and greases is the oil soluble characteristic of both components of the product. For lubricating applications, the product mixture affords economical advantages in the preparation process, as well as yields superior product characteristics.

The reaction mixtures are particularly useful for enhancing the extreme pressure properties of lubricants when added to lubricating compositions in the amount of 0.1 to 10.0 percent based on the weight of the lubricating composition. For ease of incorporation into the lubricating formulation, the reaction mixture can be diluted with a diluent compatible with the lubricating formulation. A preferred diluent is 2-hydroxyethyloctadecylimidazole, especially for reaction mixtures that are viscous.

The base oil of the lubricants may be selected from naphthenic, aromatic, paraffinic, mineral and synthetic oils. The synthetic oils may be selected from, among others, alkylene polymers, polysiloxanes, carboxylic acid esters and polyglycol ethers.

The lubricating compositions may contain the necessary ingredients to formulate the composition, as for example emulsifiers, dispersants and viscosity improvers. Greases may be prepared by adding thickeners, as for example, salts and complexes of fatty acids, polyurea compounds, clays and quaternary ammonium bentonite complexes. Depending on the intended use of the lubricant, other functional additives may be added to enhance a particular property of the lubricant. The lubricating compositions may further contain extreme pressure agents, metal passivators, rust inhibitors, dispersants and other known antioxidants and antiwear agents.

The following examples are given for the purpose of further illustrating the invention. All percentages and parts are based on weight unless otherwise indicated.

EXAMPLE 1

A reaction vessel was charged with bismuth naphthenate, 150 g, 0.129 moles Bi (18% Bismuth Nap-all™ manufactured by OM Group, Inc.) and diamylamine, 60.8 g, 0.387 moles. Carbon disulfide, 31.5 g, 0.41 moles, was slowly added with cooling to maintain temperature below 30° C. The reaction was stirred for one hour and allowed to stand overnight. Then the reaction was heated for 3 hours at 75° C. and stripped under vacuum for 10 minutes at 80° C. The yield was 239 g of a mixture of bismuth diamyldithiocarbamate and zinc naphthenate. The reaction mixture contains 11.3 percent bismuth (theoretical).

EXAMPLE 2

A reaction vessel was charged with 18% bismuth Nap-all, 205.51 g, 0.18 moles Bi and zinc diamyldithiocarbamate, 142.83 g, 0.27 moles and reacted at room temperature to yield bismuth diamyl-dithiocarbamate and zinc naphthenate. The reaction mixture contained 10.6 percent bismuth (theoretical).

EXAMPLE 3

A reaction vessel was charged with diamylamine, 65.2 g, tall oil 1-hydroxyethyl-2-imidazoline, 145 g, and bismuth 2-ehtylhexyl-carboxylate, 103.3 g. Carbon disulfide, 45 g, was charged with cooling to control the exothermic reaction and then was maintained at 80° C. The reaction was stripped under vacuum to yield bismuth diamyldithiocarbamate and imidazoline salt of 2-ethylhexyl-carboxylate.

EXAMPLE 4

A reaction vessel was charged with diamylamine, 65.2 g, and bismuth 2-ethylhexylcarboxylate, 103.3 g. Carbon disulfide, 45 g, was charged with cooling and then heated to a temperature of 80° C. The reaction was stripped under vacuum. The reaction product was bismuth diamyldithiocarbamate in 2-ethylhexyl carboxylic acid. The carboxylic acid was converted to the imidazoline salt by adding tall oil 1-hydroxyethyl-2-imidazoline, 148.6 g.

EXAMPLE 5

Four-Ball Wear Test

The wear preventive characteristics of additives of the invention were tested in lithium 12-OH stearate grease essentially according to the method described in ASTM D 2266-91. Four highly polished steel balls 12.7 mm in diameter were placed in the tester and about 5 g test sample was placed in the ball pot. The test was conducted at a rotation speed of 1200 rpm under a load of 40 kg at 75° C. The minimum scar diameter was measured to the nearest 0.01 mm.

The grease contained additives of the invention referenced in Table I. Sample A was a control grease containing no additive. Sample B contained a 1:1 mixture of bismuth diamyldithiocarbamate and zinc 2-ethylhexoate diluted with 2-hydroxyethyl-octadecylimidazole to produce 38 percent active product with a bismuth content of 8.3 percent.

TABLE I

| | Four-Ball Wear Test | | |
|---|---|---|---|
| Sample | Active Ingredient | Mass Percent | Scar Diameter, mm |
| A | — | — | 0.70 |
| B | Bi/Zn compounds 8.3% Bi | 3.42 | 0.66 |

EXAMPLE 6

Extreme-Pressure Tests

The load carrying properties of lithium 12-OH stearate grease containing the compounds of the invention were tested essentially according to the method described in ASTM D 2596-93. The test was conducted at a rotating speed of 1800 rpm at 27+/-8° C. The test samples were subjected to a series of tests of 10 second duration at increasing loads until welding of the balls occurred. The weld point measured in kgf indicates that the extreme pressure level of the grease has been exceeded.

In a second test, the load carrying capacity of the grease was determined by the Timken method conducted essentially according to the ASTM D2509-93 procedure. The tester was operated with a steel cup rotating against a steel test block at 800 rpm and about 24° C. The load carrying capacity was measured in kg after 10 min. The test samples contained additives referenced in Table II. Sample D contained a control grease with no additives. Sample E contained the additive B described in Example 5. Sample F contained a mixture of 55% bismuth dithiocarbamate and 45% zinc 2-ethylhexoate, that is, a bismuth content of 12.6%.

TABLE II

| | | Extreme-Pressure Test | | |
|---|---|---|---|---|
| Sample | Active Ingredient | Percent | Weld Point, kgf | Timken, kg |
| D | — | — | 160 | 4.54 |
| E | Bi/Zn compounds, 8.3% Bi | 2.0 3.42 | 315 — | — 36 |
| F | Bi/Zn compounds, 12.6% Bi | 2.0 2.15 | 400 — | — 27 |

The above embodiments have shown various aspects of the present invention. Other variations will be evident to those skilled in the art and such modifications are intended to be within the scope of the invention as defined by the appended claims.

What is claimed is:

1. A method for preparation of reaction mixtures by exchange reaction and comprising bismuth dithiocarbamates of the formula

$$Bi[S-\underset{\underset{\|}{S}}{C}-\underset{\underset{|}{R}}{N}-R^1]_3$$

wherein R and $R^1$ are hydrocarbyl groups selected independently from alkyl, alkenyl, cycloalkyl, aryl, alkaryl and arylalkyl groups and metal carboxylates of the formula

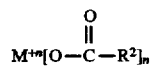

$$M^{+n}[O-\underset{\underset{\|}{O}}{C}-R^2]_n$$

wherein M represents a metal selected from alkali metals, group IIA and group IIB metals, n is 1 or 2, and $R^2$ is an alkyl or alkenyl group, naphthetic radical, or fatty radical having 8 to 22 carbon atoms comprising the steps of (1) reacting a secondary amine of the formula

$$R^1-\underset{\underset{|}{R}}{N}H$$

wherein R and $R^1$ represent groups defined above, with carbon disulfide and monovalent or divalent metal hydroxide or oxide to form the corresponding metal dithiocarbamate intermediate, (2) adding bismuth carboxylate of the formula

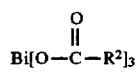

$$Bi[O-\underset{\underset{\|}{O}}{C}-R^2]_3$$

wherein $R^2$ represents the groups defined above, (3) heating at 25° to 120° C. to produce said reaction mixture, wherein the mole ratio of the bismuth dithiocarbamate to the metal carboxylate is about 1:1 to 1.5:1.

2. The method according to claim 1 wherein the exchange reaction is conducted in the presence of an inert solvent.

3. The method according to claim 1 wherein the bismuth carboxylate is derived from tall oil fatty acid.

4. The method according to claim 1 wherein the bismuth carboxylate is derived from naphthenic acid.

5. The method according to claim 1 wherein the reaction mixture contains zinc carboxylate.

6. A method for preparation of reaction mixtures by an exchange reaction and comprising bismuth dithiocarbamates of the formula

  (I)

wherein R and $R^1$ are hydrocarbyl groups selected independently from alkyl, alkenyl, cycloalkyl, aryl, alkaryl and arylalkyl groups and compounds of the formulae

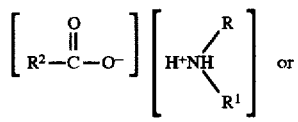  or

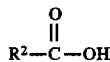  (III)

wherein $R^2$ is an alkyl or alkenyl group, naphthetic radical, or fatty radical having 8 to 22 carbon atoms comprising the steps of (1) reacting a secondary amine of the formula $R^1$-NH-R wherein R and $R^1$ represent groups defined above, with carbon disulfide in a mole ratio of about 2:1 to form the corresponding dithiocarbamate amine salt intermediate.

(2) adding bismuth carboxylate of the formula

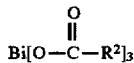  (IV)

wherein $R^2$ represents the groups as defined above, (3) heating at 25° to 1200° C. to produce a reaction mixture wherein the mole ratio of the bismuth dithiocarbamate of formula (I) and the amine salt of carboxylic acid of formula (II) is about 1:1 to 1.5:1, (4) adding one mole of carbon disulfide and one-third mole of bismuth carboxylate of formula IV, (5) heating at 25° to 1200° C. to produce a reaction mixture wherein the mole ratio of the bismuth dithiocarbamate of formula (I) and carboxylic acid of formula (II) is about 2:1 to 2.5:1.

7. The method according to claim 6 wherein the exchange reaction is conducted in the presence of an inert solvent.

8. A method for preparation of reaction mixtures by an exchange reaction and comprising bismuth dithiocarbamates of the formula

wherein R and $R^1$ are hydrocarbyl groups selected independently from alkyl, alkenyl, cycloalkyl, aryl, alkaryl and arylalkyl groups and amine salts of carboxylates of the formula

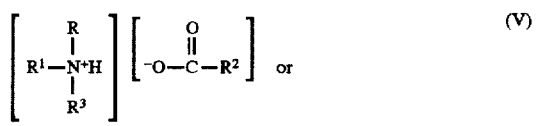  (V)

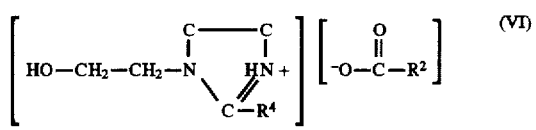  (VI)

wherein $R^3$ represents hydrogen, R or $R^1$ as defined above, $R^4$ is alkyl, alkenyl or fatty residue having 8 to 22 carbon atoms, comprising the steps of (1) reacting a secondary amine of the formula

wherein R and $R^1$ represent groups defined above, with carbon disulfide and an amine of the formula VII or VIII

  (VII)

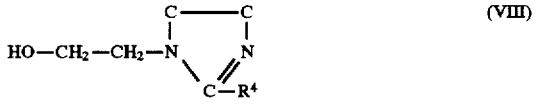  (VIII)

wherein R, $R^1$, $R^3$ and $R^4$ represent groups defined above, to form the corresponding amine dithiocarbamate intermediate, (2) adding bismuth carboxylate of the formula

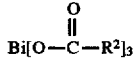

wherein $R^2$ represents the groups defined above, (3) heating at 25° to 120° C. to produce said reaction mixture wherein the mole ratio of the bismuth dithiocarbamate to the amine carboxylate is about 1:1 to 1.5:1.

* * * * *

UNITED STATES PATENT AND TRADEMARK OFFICE
CERTIFICATE OF CORRECTION

PATENT NO.   : 5,631,214
DATED        : May 20, 1997
INVENTOR(S)  : Thomas J. Karol and Steven G. Donnelly It is certified that error appears in the above-indentified patent and that said Letters Patent is hereby corrected as shown below:

At column 2, line 21, column 7, line 42, and column 7, line 49

"1200° C" should read --120°C--.

Signed and Sealed this

Second Day of September, 1997

Attest:

BRUCE LEHMAN

Attesting Officer                Commissioner of Patents and Trademarks